United States Patent [19]

Johnson et al.

[11] Patent Number: 5,596,103

[45] Date of Patent: Jan. 21, 1997

[54] PROCESS FOR PREPARING BENZOPYRAN COMPOUNDS

[75] Inventors: Graham Johnson, Worthing; Neil Smith, Shoreham-by-Sea; Graham R. Geen, Stansted Mountfitchet; Inderjit S. Mann, Welling, all of England; Vance Novack, Devon, Pa.

[73] Assignee: SmithKline Beecham Plc, England

[21] Appl. No.: 451,843

[22] Filed: May 26, 1995

Related U.S. Application Data

[63] Continuation of PCT/EP93/03257, Nov. 19, 1993, published as WO94/12492, Jun. 9, 1994.

[30] Foreign Application Priority Data

Nov. 27, 1992 [GB] United Kingdom ............... 9224922

[51] Int. Cl.$^6$ ............... C07D 257/04; C07D 407/04
[52] U.S. Cl. ............................. 548/253; 548/252
[58] Field of Search ....................... 548/252, 253

Primary Examiner—David B. Springer
Attorney, Agent, or Firm—James M. Kanagy; Stephen Venetianer; Edward T. Lentz

[57] ABSTRACT

This invention comprises a process for preparing benzopyran derivatives represented by formula (I)

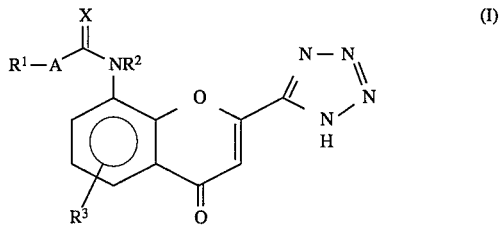

in which, $R^1$ is $C_{1-20}$alkyl, $C_{2-20}$alkenyl, $C_{2-20}$alkynyl, or a group of structure (i), (ii) or (iii).

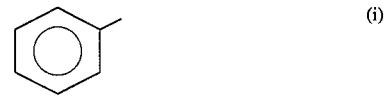

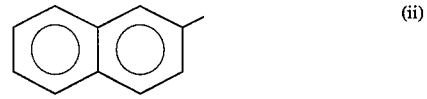

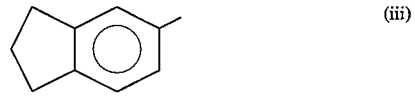

2 Claims, No Drawings

PROCESS FOR PREPARING BENZOPYRAN COMPOUNDS

This is a continuation of PCT application Ser. No. PCT/EP93/03257 filed 19 Nov. 1993 which claimed priority from GB Application 9224922.6 filed 27 Nov. 1992, now abandoned.

The present invention relates to a new process for preparing certain substituted benzopyran compounds, intermediates useful in the process, and to a process for the preparation of the intermediates.

Substituted benzopyran compounds are known in the art. For example, EP 0 173 516-A discloses a class of substituted benzopyran compounds which are described as compounds having activity as leukotriene antagonists and useful in therapy in the treatment of, for example, diseases induced by leukotrienes and 5-α-reductase.

The present invention relates to a new process for preparing certain of the benzopyran compounds described in EP 0 173 516-A, and in particular provides an efficient route to the compounds in which far fewer reaction steps are involved than has hitherto been described. A reduction in the number of reaction steps involved in preparing end products generally results in a much more efficient and cost-effective route than one involving large numbers of steps.

The present invention therefore provides in a first aspect a process for preparing a compound of structure (I):

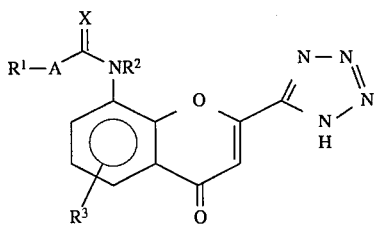

(I)

in which, $R^1$ is $C_{1-20}$alkyl, $C_{2-20}$alkenyl, $C_{2-20}$alkynyl, or a group of structure:

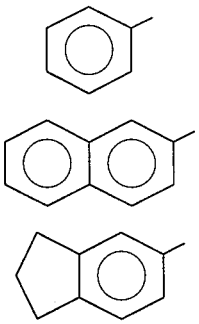

(i)

(ii)

(iii)

each of which may be substituted by one or two substituents selected independently from $C_{1-20}$alkyl, $C_{2-20}$alkenyl or $C_{2-20}$alkynyl, up to 5 carbon atom(s) of which may optionally be replaced by oxygen atom(s), sulphur atom(s), halogen atom(s), nitrogen atom(s), benzene ring(s), thiophene ring(s), naphthalene ring(s), carbocyclic ring(s) of from 4 to 7 carbon atom(s), carbonyl group(s), carbonyloxy group(s), hydroxy group(s), carboxy group(s), azido group(s) and/or nitro group(s);

$R^2$ is hydrogen or $C_{1-6}$alkyl;

$R^3$ is hydrogen, halogen, hydroxy, nitro, a group of general formula —COOR$^4$ (wherein R$^4$ represents hydrogen or $C_{1-6}$alkyl), $C_{1-6}$alkyl, $C_{1-6}$alkoxy or $C_{1-6}$alkylthio;

A is a single bond or a methylene, ethylene, trimethylene, tetramethylene, vinylene, propenylene, butenylene, butadienylene or ethynylene group optionally being substituted by one, two or three $C_{1-10}$alkyl and/or phenyl group(s); and X is oxygen or sulphur;

or a salt, solvate or hydrate thereof, which comprises cyclisation of a compound of structure (II)

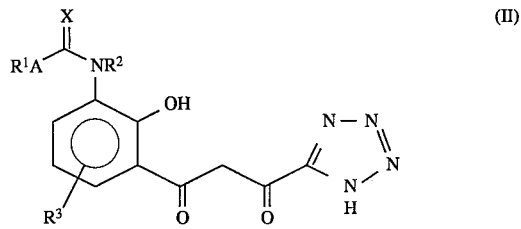

(II)

or a salt, hydrate or solvate thereof, in which $R^1$, $R^2$, $R^3$, A and X are as described for structure (I), and optionally thereafter forming a salt, solvate or hydrate thereof.

Suitably, $R^1$ is $C_{1-20}$alkyl, $C_{2-20}$alkenyl, $C_{2-20}$alkynyl, or a group of structure:

(i)

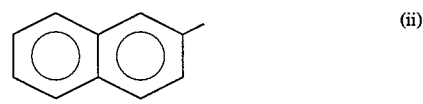

(ii)

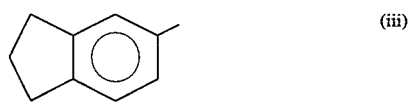

(iii)

each of which may be substituted by one or two substituents selected independently from $C_{1-20}$alkyl, $C_{2-20}$alkenyl or $C_{2-20}$alkynyl, up to 5 carbon atom(s) of which may optionally be replaced by oxygen atom(s), sulphur atom(s), halogen atom(s), nitrogen atom(s), benzene ring(s), thiophene ring(s), naphthalene ring(s), carbocyclic ring(s) of from 4 to 7 carbon atom(s), carbonyl group(s), carbonyloxy group(s), hydroxy group(s), carboxy group(s), azido group(s) and/or nitro group(s).

Preferably $R^1$ is a group of structure (i) substituted or unsubstituted by one or two substituents selected independently from $C_{1-20}$alkyl, $C_{2-20}$alkenyl or $C_{2-20}$alkynyl, up to 5 carbon atom(s) of which may optionally be replaced by oxygen atom(s), sulphur atom(s), halogen atom(s), nitrogen atom(s), benzene ring(s), thiophene ring(s), naphthalene ring(s), carbocyclic ring(s) of from 4 to 7 carbon atom(s), carbonyl group(s), carbonyloxy group(s), hydroxy group(s), carboxy group(s), azido group(s) and/or nitro group(s).

More preferably $R^1$ is a group of structure (i) substituted in the para position of the ring by a single substituent selected from the above, in particular $R^1$ is a group of structure

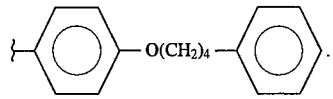

Suitably, $R^2$ is hydrogen or $C_{1-6}$alkyl; preferably $R^2$ is hydrogen.

Suitably, $R^3$ is hydrogen, halogen, hydroxy, nitro, a group of general formula —COOR$^4$ (wherein R$^4$ represents hydrogen or $C_{1-6}$alkyl) or $C_{1-6}$alkyl, $C_{1-6}$alkoxy or $C_{1-6}$alkylthio. Preferably $R^3$ is hydrogen.

Suitably A is a single bond or a methylene, ethylene, trimethylene, tetramethylene, vinylene, propenylene, butenylene, butadienylene or ethynylene group optionally being substituted by one, two or three $C_{1-10}$alkyl and/or phenyl group(s). Preferably A is a single bond.

Suitably, the cyclisation of the compound of structure (II) is carried out in the presence of an acid. For example, the cyclisation can be carried out in the presence of sulphuric acid, in methanol or in acetic acid as the solvent reedinto. Preferably the reaction is carried out in a methanol/tetrahydrofuran solvent mixture in the presence of hydrochloric acid. Alternative acid/solvent conditions will be apparent to those skilled in the art and include, for example, acids such as hydrobromic or hydroiodic acid, perchloric acid or p-toluene sulphonic acid, and Lewis Acids for example aluminium trichloride, in suitable solvents such as water, $C_{1-4}$alkanols such as ethanol or methanol, and unsaturated carbocyclic hydrocarbons such as benzene or toluene.

It is to be noted that, although for the sake of convenience structure (II) is represented as the 'di-keto' form, the compounds of structure (II) can exist also in the 'keto-enol' form and in the 'cyclic hydroxy chromanone' form (IIB)

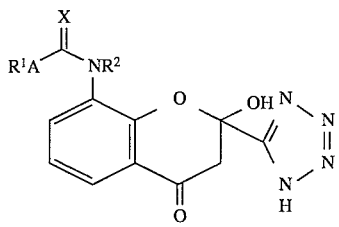
(IIB)

It is intended that structure (II) encompasses all of the tautomeric forms of the compounds of structure (II).

In a preferred aspect there is therefore provided a process for the preparation of a compound of structure (IA) or a salt, solvate or hydrate thereof:

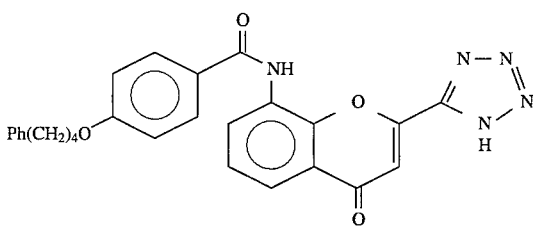
(IA)

which comprises cyclisation of a compound of structure (IIA) or a salt, solvate or hydrate thereof:

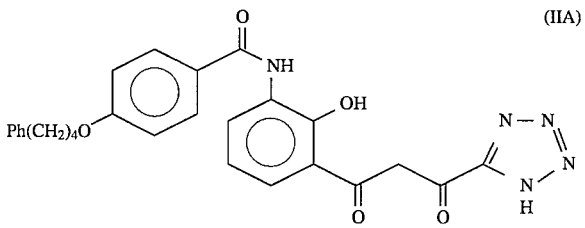
(IIA)

and optionally thereafter forming a salt, solvate or hydrate thereof. Most preferably, the cyclisation is carried out in the presence of hydrochloric acid in methanol/tetrahydrofuran as solvent, As for compounds of structure (II), the compounds of structure (IIA) can, of course, exist in the corresponding keto-enol and cyclic chromanone forms, each of which are intended to be encompassed by the structure (IIA).

The compounds of structure (II) (and in particular structure (IIA)) are novel and fore a further aspect of the invention. The compounds of structure (II) can be prepared by the reaction of a compound of structure (III)

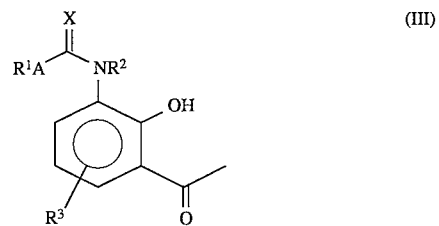
(III)

in which $R^1$, $R^2$, $R^3$, A and X are as described for structure (I) in claim 1 with a compound of structure (IV) or a salt thereof

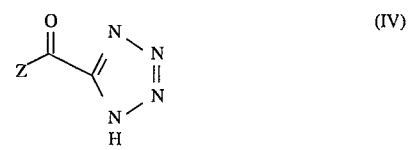
(IV)

in which Z is an activated leaving group.

Suitably, activated leaving groups Z include, for example, activated amides of structure $N(R^5)(OR^5)$ in which $R^5$ is $C_{1-6}$alkyl, halogen groups, groups of structure $R^6O$, $R^6S$ or $R^6SO_2O$ in which $R^6$ is $C_{1-6}$alkyl, optionally substituted phenyl or optionally substituted phenyl$C_{1-6}$alkyl, or groups of structure

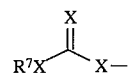

in which $R^7$ is $C_{1-6}$alkyl, optionally substituted phenyl or optionally substituted phenyl$C_{1-6}$alkyl, and each group X is, independently, oxygen or sulphur. Preferably Z is $R^6O$.

Suitably, $R^6$ is $C_{1-6}$alkyl, optionally substituted phenyl or optionally substituted phenyl$C_{1-6}$alkyl. Preferably, $R^6$ is $C_{1-6}$alkyl, for example, methyl, ethyl, i-butyl or t-butyl; most preferably $R^6$ is ethyl.

Suitably, the reaction is carried out in an organic solvent such as for example, dimethylformamide, ethereal solvents such as tetrahydrofuran, toluene or benzene, hexanes or $C_{1-6}$alkanols such as methanol or ethanol, in the presence of a base, for example an alkali metal alkoxide such as potassium t-butoxide, sodium methoxide or potassium methoxide, hydrides such as sodium hydride, or an amide base such as potassium amide or sodium amide. Preferably, the reaction is carried out in tetrahydrofuran as a solvent in the presence of sodium methoxide as a base.

The process for preparing the compounds of structure (II) is novel and forms a further aspect of the invention. In particular, the process is preferred to be used in the preparation of the compounds of structure (IIA) by reaction of the following compounds of structure (IIIA) and a compound of structure (IVA) or a salt thereof, in the presence of sodium methoxide in tetrahydrofuran as a solvent:

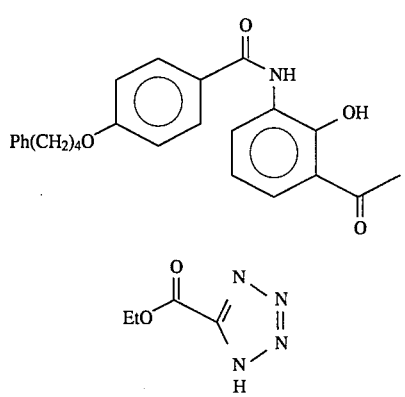

The compounds of structure (III) and (IV) are prepared from commercially available starting materials by standard techniques as hereinafter described. For example, the preparation of compounds of structure (III) is described in EP 0 173 516-A. Compounds of structure (IV), for example in which Z is $R^6O$, can be prepared from sodium azide and an appropriate alkyl cyanoformate such as ethyl cyanoformate by known methods or from tetrazole-5-carboxylic acid disodium salt (commercially available) by reaction with the appropriate alkyl, aryl or arylalkyl haloformate, for example, ethylchloroformate or isobutylchloroformate. The preparation of compounds of structure (IV) from the corresponding tetrazole-5-carboxylic acid disodium salt is novel and forms a still further aspect of the invention. It is to be noted that the compounds of structure (IV) can be prepared and then isolated before reaction with appropriate compounds of structure (III), or can be prepared 'in situ' and further reacted with the compounds of structure (III) without prior isolation.

The present invention is in particular useful in the preparation of the compounds of structure (IA) beginning from compounds (IIIA) and (IVA) to form the intermediates of structure (IIA) which undergo cyclisation under the conditions described herein to form the desired product. The compounds of structure (II) can be isolated from the reaction mixture before cyclisation to the compounds of structure (I) or alternatively, as described in the examples, the reaction between compounds of structures (III) and (IV) followed by the cyclisation of the compounds of structure (II) so formed can be carried to completion in 'one pot', that is to say without the isolation of the intermediates so formed.

The following examples serve to illustrate the invention. Temperatures are recorded in degrees Celsius (°C.).

EXAMPLES

1. Preparation of Ethyl-1H-Tetrazole-5-Carboxylate

Trifluoroacetic acid (24.47 g, 0.21M) was added dropwise over 0.5 hr under nitrogen to a stirred suspension of sodium azide (12.59 g, 0.19M) in 2,6-lutidine (100 ml) at 8° to 12°. After stirring for 7 minutes ethyl cyanoformate (20.4 g, 0.20M) was added in one portion. The mixture was heated and stirred at 75° for 6 hours and then, after cooling, stirred at 20° for 16 hr. After cooling to 10° the mixture was added to ice (250 g) and 11 molar hydrochloric acid (100 ml) keeping the temperature below 20°. The product was extracted into ethyl acetate (1×250, 1×200, 2×100 ml) and the combined extracts dried over magnesium sulphate. After evaporation of the solvent under reduced pressure the oily product (38.22 g) was taken up in ether (50 ml) and hexane (25 ml) added. Storage at 4° for 2–3 days produced crystalline ethyl-1H-tetrazole-5-carboxylate that was filtered off, washed with chilled ether, and air dried, 14.12 g (52.6% yield), m.p. 88°–93°.

NMR: (270 MHz, solution in $CDCl_3$) δ13.6–13.8 (s, 1H); 4.6–4.5 (q, 2H); 1.5–1.4 (t, 3H).

Workup variation

On a larger scale (83.4 g sodium azide) the reaction was worked up differently in order to prevent the liberation of any hydrazoic acid.

After stirring at 75° and 20° a solution of sodium nitrite (63 g) in water (300 ml) was added over 10 minutes at 20° to 30°. The mixture was stirred at 20°–25° for 20 minutes and then a chilled mixture of water (1.5 L) and 11 molar hydrochloric acid (690 ml) added keeping the temperature between 25° and 30°. The product was then extracted into ethyl acetate and crystallised as described above.

2. Preparation of i-Butyl-1H-Tetrazole-5-Carboxylate

To a stirred suspension of tetrazole-5-carboxylic acid disodium salt (15.8 g, 0.1 mol) in dimethylformamide (100 ml) under a nitrogen atmosphere at 5° was added isobutyl chloroformate (13.6 g, 13 ml, 0.1 mol) dropwise over 15 minutes. The mixture was stirred at 5°–10° for 2 hours, then at 20° for 2 hours. The mixture was added to water (500 ml) and extracted with ethyl acetate (2×200 ml). The aqueous phase was then acidified to pH1 with conc. HCl and further extracted with ethyl acetate (2×200 ml). The latter extracts were washed with water (2×200 ml), dried ($MgSO_4$) and evaporated to give the title compound as a gnm (8.6 g, 50.5%).

$^1H$ NMR ($CDCl_3$): δ0.95 (d, 6H, $CH_3$), 2.08 (tq, 1H, CH), 4.25 (d, 2H, $CH_2$).

3. Preparation of Methyl 4-(4-Phenylbutoxy)benzoate

A solution of methyl 4-hydroxybenzoate (13.4 kg, 88 mol) in DMF (52 L) was added dropwise to a mixture of NaOMe (4.8 kg, 89 mol) and DMF (50 L) at room temperature under a gentle stream of nitrogen. The reaction mixture was heated at 60°–70° for 1 hr with stirring and then cooled to room temperature. To this mixture was added dropwise a solution of 4-phenylbutyl bromide (16.92 kg, 79.4 mol) in DMF (5 L). The resulting mixture was heated at 60°–70° for 1 hr with constant stirring and cooled to room temperature. After an addition of 1N-NaOH (110 L) was added, and the product was extracted twice with ethyl acetate (50 L and 80 L). The extracts were washed with 1N-NaOH (110 L) and saturated brine (20 L) successively, and then concentrated to dryness in vacuo to give the title compound in quantitative yield.

4. Preparation of 4-(4-Phenylbutoxy)benzoic Acid

To a solution of the compound from Example 3 in MeOH (50 L) was added 3N-NaOH (46 L). The mixture was heated under reflux for 1.5 hrs. Upon termination of the reaction, the MeOH was removed by distillation in vacuo. Ice-water (120 L) was added to the residue, and the neutral materials were extracted with ether (30 L×3). The combined ethereal extracts were washed with 2N-NaOH (25 L). The aqueous layers were combined and adjusted to pH 2–3 with concentrated HCl (16 L). Precipitated solids were collected by centrifugal filtration, washed with water and dried by heating at 70°–80° under a stream of air to obtain the title compound, (17.67 kg, 65.4 mol, 2% yield from 4-hydroxybenzoate).

5. Preparation of 3-[4-(4-Phenylbutoxy)benzoylamino]-2-hydroxyacetophenone

To a solution of the compound from Example 4 (18.1 g, 67 mmol) in CH$_2$Cl$_2$ (45 ml) was added a catalytic amount of DMF (0.45 ml) followed by thionyl chloride (6.26 ml, 85.8 mmol) at room temperature under a stream of nitrogen. Afar reflux for 2 hr, the mixture was cooled to room temperature and was added to a solution of 3'-amino-2'-hydroxyacetephenone hydrochloride (12 g, 64 mmol) and pyridine (15.5 ml, 192 mmol) in CH$_2$Cl$_2$ (90 ml) while maintaining the temperature between 0°–3°. The mixture was stirred at 0°–3° for 2 hr, and poured into 2N-HCl (200 ml). The aqueous layer was separated. The product in aqueous layer was extracted twice with CH$_2$Cl$_2$ (150 ml and 100 ml). The CH$_2$Cl$_2$ layers were combined, washed successively with water, saturated NaHCO$_3$ (150 ml), and saturated brine (150 ml), dried over MgSO$_4$. The resulting solution was concentrated in vacuo until some of the crystals were precipitated. Ethyl acetate (150 ml) was added to the residue, and the solution was concentrated in vacuo until about a half of the ethyl acetate was distilled out. The mixture was cooled to approximately 0°. Precipitated crystals were collected by filtration and dried in vacuo to afford the title compound, (21.6 g, 53.6 mmol, 90% yield).

6. Preparation of 2-[4-(4-Phenylbutoxy)benzoylamino]-6-[1,3-dioxo-3-(tetrazol-5-yl)propyl]phenol Under a nitrogen atmosphere, potassium tert-butoxide (31.36 g, 0.28 mol) was dissolved in dry DMF (160 ml) by sting. To the resulting solution were added the hydroxy acetophenone compound from Example 5 (16.12 g, 0.04 mol) followed by 5-ethoxycarbonyl tetrazole from Example 1 (7.39 g, 0.052 mol, 1.3 equiv.) at room temperature. The reaction temperature rises to approximately 45°. The mixture was stirred for 3 hours at 40° (off bath), then cooled to 30° and poured into cold 1N HCl (800 ml). The resulting precipitate was filtered, washed with water (500 ml), and then dried at 70° in a fan oven to obtain the title compound (19.4 g, 97%). Purification was carried out using either of the following procedures.

Procedure 1: A stirred slurry of crude product (10 g) in ethyl acetate (150 ml) was heated at 60° for 2 hours. After cooling to room temperature, the mixture was transferred to a refrigerator and left for 2 hours. The product was then filtered, washed with cold ethyl acetate (15 ml), and dried at 70° in a fan oven to afford purified product (8.5 g, 85%).

2: Procedure 2: A stirred slurry of crude product (5 g) in acetone (50 ml) was heated under reflux for 2 hours. Afar cooling to room temperature, the mixture was transferred to a refrigerator and left for 2 hours. The product was then filtered, washed with cold acetone (5–10 ml), and dried at 70° in a fan oven to afford purified product (4.1 g, 82%).

7. Preparation of 4-OXo-8-[4-(4-phenylbutoxy)benzoylamino]-2-tetrazol-5-yl-4H-1-benzopyran hemihydrate To a stirred slurry of purified product from Example 6 (7.984 g, 0.016 mol) in methanol (72 ml) was added concentrated sulphuric acid (0.6 m), and the reaction heated to reflux and stirred for 3 hours. The mixture was allowed to cool to room temperature and then transferred to a refrigerator for 2 hours. The thick mixture was then filtered, washed with cold methanol (40 ml) and water (90 ml) followed again by cold methanol (30 ml). The product was dried at 70° in a fan oven and then left to stand for 24 hours at room temperature to afford the rifle compound (7.36 g, 96% ):

Examples 8 and 9

These two examples illustrate the 'one-pot' procedure for the preparation of compounds (I) from the intermediate compounds of structures (III) and (IV).

8. Preparation of 4-Oxo-8-[4-(4-phenylbutoxy)benzoylamino]-2-tetrazol-5-yl-4H-1-benzopyran hemihydrate.

To a stirred suspension of sodium methoxide (15 g, 0.28 mole) in dry THF under a nitrogen atmosphere was added, in portions, the hydroxyacetophenone compound from example 5 (16 g, 0.04 mole) at about 25° C. A solution of ethyl tetrazole-5-carboxylate from example 1 (7.3 g, 0.05 mole) in THF was then added while maintaining the reaction temperature at about 25° C. The reaction mixture was stirred at reflux for about 100 minutes to ensure complete formation of the diketone compound from example 6. Methanol was added to the reaction mixture followed by concentrated hydrochloric acid (28 ml, 0.34 mole), and subsequent heating of the reaction mixture at reflux for about 2 hours resulted in the formation of the title compound which crystallised out of solution. After cooling to about 20° C., the product was isolated by filtration and washed with methanol. The isolated solid was purified by conversion to the sodium salt in methanol and reprecipitating the title compound with hydrochloric acid. The reprecipitated product was isolated by filtration, washed with aqueous methanol, dried and then rehydrated at room temperature to give the title compound (18.56 g, 94%).

9. Preparation of 4-Oxo-8-[4-(4-phenylbutoxy)benzoylamino]-2-tetrazol-5-yl-4H-1-benzopyran hemihydrate.

To a stiffed suspension of sodium methoxide (14.1 kg, 261 mole)in dry THF under a nitrogen atmosphere. was added, in portions, the hydroxyacetophenone compound from example 5 (15.0 kg, 37.2 mole) at about 25° C. A solution of ethyl tetrazole-5-carboxylate from example 1 (6.8 kg, 47.9 mole) in THF was then added while maintaining the reaction temperature at about 25° C. The reaction mixture was stirred at reflux for about 100 minutes to ensure complete formation of the diketone compound from example 6. Methanol was added to the reaction mixture followed by concentrated hydrochloric acid (31.4 kg, 314 mole), and subsequent heating of the reaction mixture at reflux for about 2 hours resulted in the formation of the title compound which crystallised out of solution. After cooling to about 20° C., the product was isolated by filtration and washed with methanol. The isolated solid was purified by conversion to the sodium salt in methanol and reprecipitating the title compound with hydrochloric acid. The reprecipitated product was isolated by filtration, washed with aqueous methanol, dried and then rehydrated at room temperature to give the title compound (15.5 kg, 85%).

We claim:

1. A process for preparing a compound of structure (IA):

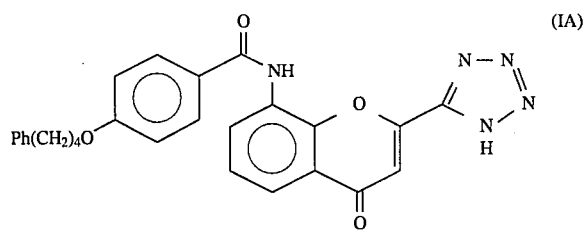

(IA)

or a salt, hydrate or solvate thereof, which comprises reacting a compound of structure (IIIA) with a compound of structure (IVA) or a salt thereof in an organic solvent in the presence of a base:

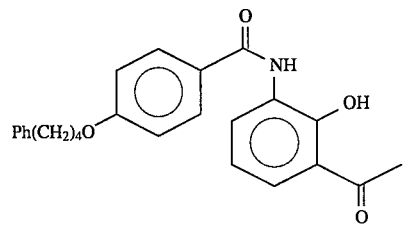

(IIIA)

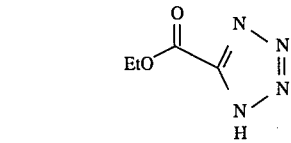

(IVA)

followed by cyclisation of the intermediate compound of structure (IIA) in the presence of an acid or a Lewis acid in a compatible solvent

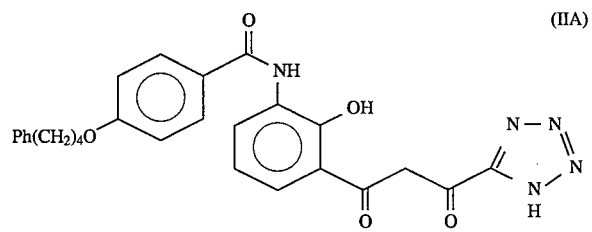

(IIA)

or a salt, hydrate or solvate thereof, so formed.

2. A process for preparing a compound of structure (IV):

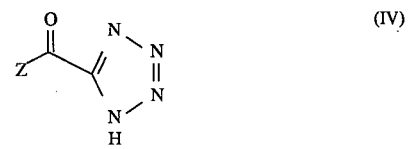

(IV)

in which Z is a group $R^6O$ in which $R^6$ is $C_{1-6}$alkyl, optionally substituted phenyl or optionally substituted phenyl$C_{1-6}$alkyl, which comprises reaction of tetrazole-5-carboxylic acid disodium salt with the appropriate alkyl, aryl or arylalkyl haloformate.

* * * * *